(12) United States Patent
Torres-Ordonez et al.

(10) Patent No.: US 10,301,563 B2
(45) Date of Patent: *May 28, 2019

(54) OXYGENATED BUTANOL GASOLINE COMPOSITION HAVING GOOD DRIVEABILITY PERFORMANCE (71) Applicant: BUTAMAX ADVANCED BIOFUELS LLC, Wilmington, DE (US)

(72) Inventors: Rowena Justo Torres-Ordonez, Naperville, IL (US); Melanie Kuberka, Essen (DE); Peter Placzek, Gladbeck (DE); Leslie R. Wolf, Naperville, IL (US); James J. Baustian, St. Charles, IL (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/179,469

(22) Filed: Jun. 10, 2016

(65) Prior Publication Data
US 2016/0281012 A1 Sep. 29, 2016

Related U.S. Application Data (60) Continuation of application No. 14/497,682, filed on Sep. 26, 2014, now Pat. No. 9,388,353, which is a
(Continued)

(51) Int. Cl.
C10L 1/00 (2006.01)
C10L 1/182 (2006.01)
(Continued)

(52) U.S. Cl.
CPC .............. *C10L 1/1824* (2013.01); *C10L 1/023* (2013.01); *C10L 1/06* (2013.01); *G01N 33/22* (2013.01);
(Continued)

(58) Field of Classification Search
CPC .......... C10L 1/1824; C10L 1/023; C10L 1/06; C10L 2200/0423; C10L 2200/0469;
(Continued)

(56) References Cited

U.S. PATENT DOCUMENTS

| 1,570,060 A | 1/1926 | Hammond |
| 1,713,530 A | 5/1929 | Hammond |

(Continued)

FOREIGN PATENT DOCUMENTS

| WO | 2006081089 | 8/2006 |
| WO | 2009102608 | 8/2009 |
| WO | 2009137356 | 11/2009 |

OTHER PUBLICATIONS

International Search Report and Written Opinion of corresponding PCT/US2011/040716 dated Sep. 19, 2011.
(Continued)

Primary Examiner — Cephia D Toomer (57) ABSTRACT

Gasoline blends and methods for producing gasoline blends containing high concentrations of a butanol isomer and having good cold start and warm-up driveability characteristics are disclosed.

8 Claims, 5 Drawing Sheets

Related U.S. Application Data division of application No. 13/162,206, filed on Jun. 16, 2011, now Pat. No. 8,876,924.

(60) Provisional application No. 61/355,222, filed on Jun. 16, 2010.

(51) Int. Cl.
    *C10L 1/02* (2006.01)
    *C10L 1/06* (2006.01)
    *G01N 33/22* (2006.01)

(52) U.S. Cl.
    CPC .......... *C10G 2300/104* (2013.01); *C10G 2300/1014* (2013.01); *C10G 2300/1044* (2013.01); *C10G 2300/30* (2013.01); *C10G 2300/301* (2013.01); *C10G 2300/304* (2013.01); *C10L 2200/0423* (2013.01); *C10L 2200/0469* (2013.01); *C10L 2270/023* (2013.01); *Y02P 30/20* (2015.11)

(58) Field of Classification Search
    CPC ...... C10L 2270/023; C10G 2300/1014; C10G 2300/30; C10G 2300/304; C10G 2300/104; C10G 2300/1044; C10G 2300/301; G01N 33/22; Y02P 30/20
    See application file for complete search history.

(56) References Cited

U.S. PATENT DOCUMENTS

| | | |
|---|---|---|
| 1,774,180 A | 8/1930 | Mann |
| 4,039,301 A | 8/1977 | Laity |
| 4,066,419 A | 1/1978 | Wharton |
| 4,316,724 A | 2/1982 | Herbstman |
| 4,468,233 A | 8/1984 | Bruderreck et al. |
| 4,541,836 A | 9/1985 | Derderian |
| 5,401,280 A | 3/1995 | Kaneko et al. |
| 5,755,833 A | 5/1998 | Ishida et al. |
| 5,782,937 A | 7/1998 | Colucci et al. |
| 6,083,228 A | 7/2000 | Michelson |
| 6,565,617 B2 | 5/2003 | Kalghatgi |
| 6,761,745 B2 | 7/2004 | Hull et al. |
| 6,858,048 B1 | 2/2005 | Jimeson et al. |
| 8,465,560 B1 | 6/2013 | Wolf |
| 8,734,543 B2 | 5/2014 | Baustian |
| 8,870,983 B2 | 10/2014 | Baustian et al. |
| 8,876,924 B2 | 11/2014 | Torres-Ordonez et al. |
| 8,968,429 B2 | 3/2015 | Baustian et al. |
| 8,969,050 B2 | 3/2015 | Austin et al. |
| 9,217,737 B2 | 12/2015 | Boyd et al. |
| 9,359,568 B2 | 6/2016 | Baustian et al. |
| 9,388,353 B2 | 7/2016 | Torres-Ordonez et al. |
| 9,410,098 B2 | 8/2016 | D'Amore et al. |
| 9,481,842 B2 | 11/2016 | Baustian et al. |
| 9,657,244 B2 | 5/2017 | Baustian |
| 2003/0154649 A1* | 8/2003 | Hull .......... C10L 1/023 44/350 |
| 2004/0107634 A1 | 6/2004 | Binions |
| 2006/0162243 A1 | 7/2006 | Wolf |
| 2008/0261230 A1 | 10/2008 | Liao et al. |
| 2009/0099401 A1 | 4/2009 | D'Amore et al. |
| 2009/0199464 A1* | 8/2009 | Wolf .......... C10L 1/023 44/451 |
| 2009/0277079 A1 | 11/2009 | Baustian |
| 2009/0292512 A1 | 11/2009 | Wolf |
| 2010/0307053 A1 | 12/2010 | Kuberka et al. |
| 2011/0023354 A1 | 2/2011 | Wolf |
| 2011/0283604 A1 | 11/2011 | Foster et al. |
| 2013/0180164 A1 | 7/2013 | Wolf |
| 2013/0227878 A1 | 9/2013 | Wolf et al. |
| 2013/0247450 A1 | 9/2013 | Wolf |
| 2014/0109467 A1 | 4/2014 | Wolf |
| 2015/0007491 A1 | 1/2015 | Baustian et al. |
| 2015/0191686 A1 | 7/2015 | Austin et al. |
| 2016/0257900 A1 | 9/2016 | Baustian et al. |
| 2016/0335416 A1 | 11/2016 | Wolf |
| 2017/0015919 A1 | 1/2017 | Baustian et al. |

OTHER PUBLICATIONS

U.S. Appl. No. 13/162,206, filed Jun. 16, 2011.
U.S. Appl. No. 13/162,184, filed Jun. 16, 2011.
U.S. Appl. No. 14/259,611, filed Apr. 23, 2014.

* cited by examiner

OXYGENATED BUTANOL GASOLINE COMPOSITION HAVING GOOD DRIVEABILITY PERFORMANCE

CROSS-REFERENCE TO RELATED APPLICATIONS

The present application is a continuation of U.S. patent application Ser. No. 14/497,682, filed on Sep. 26, 2014 which is a divisional application of U.S. patent application Ser. No. 13/162,206, filed on Jun. 16, 2011 which claims the benefit of U.S. Provisional Patent Application No. 61/355,222, filed Jun. 16, 2010, the contents of each are fully incorporated herein by reference.

BACKGROUND OF THE INVENTION

This invention relates to fuels, more particularly to oxygenated gasolines including gasolines containing butanol. This invention provides an oxygenated butanol gasoline having good cold start and warm-up driveability performance.

Gasolines are fuels which are suitable for use in a spark-ignition engine and which generally contain as a primary component a mixture of numerous hydrocarbons having different boiling points and typically boiling at a temperature in the range of from about 79° F. to about 437° F. under atmospheric pressure. This range is approximate and can vary depending upon the actual mixture of hydrocarbon molecules present, the additives or other compounds present (if any), and the environmental conditions. Typically, the hydrocarbon component of gasolines contains C4 to C10 hydrocarbons.

Gasolines are typically required to meet certain physical and performance standards. Some characteristics may be implemented for proper operation of engines or other fuel combustion apparatuses. However, many physical and performance characteristics are set by national or regional regulations for other reasons such as environmental management. Examples of physical characteristics can include Reid Vapor Pressure, sulfur content, oxygen content, aromatic hydrocarbon content, benzene content, olefin content, the temperature at which 90 percent of the fuel is distilled (T90), the temperature at which 50 percent of the fuel is distilled (T50) and others. Performance characteristics can include octane rating, combustion properties, and emission components.

For example, standards for gasolines for sale within much of the United States are generally set forth in ASTM Standard Specification Number D 4814 ("ASTM D 4814") which is incorporated herein by reference. Standards for gasolines for sale within much of Europe are generally set forth in European Standard EN228:2008, which is also incorporated herein by reference.

Additional federal and state regulations supplement this ASTM standard. The specifications for gasolines set forth in ASTM D 4814 vary based on a number of parameters affecting volatility and combustion such as weather, season, geographic location and altitude. For this reason, gasolines produced in accordance with ASTM D 4814 are broken into volatility categories AA, A, B, C, D and E, and vapor lock protection categories 1, 2, 3, 4, 5, and 6, each category having a set of specifications describing gasolines meeting the requirements of the respective classes. These specifications also set forth test methods for determining the parameters in the specification.

For example, a Class AA-2 gasoline blended for use during the summer driving season in relatively warm climates must have a maximum vapor pressure of 7.8 psi, a maximum temperature for distillation of 10 percent of the volume of its components (the "T10") of 158° F., a temperature range for distillation of 50 percent of the volume of its components (the "T50'") of between 170° F. and 250° F., a maximum temperature for distillation of 90 percent of the volume of its components (the "T90") of 374° F., a distillation end point of 437° F., a distillation residue maximum of 2 volume percent, and a maximum "Driveability Index" or "DI", as described below, of 1250.

Cold start and warm-up (CS&W) performance is a key quality indicator for gasoline motor fuels; properly formulated gasoline fuels enable a cold engine (i.e., an engine which is essentially the same temperature as its surroundings with no residual heat from previous running) to start quickly and provide smooth drive-away performance under all climatic conditions. The startup and driveaway performance should be free from faults such as long cranking time, stalls, and stumble or hesitation on acceleration.

The CS&W performance of gasoline is controlled by the fuel's volatility properties traditionally including the vapor pressure and especially the distillation properties (that is, the distribution of component boiling temperatures across the fuel's boiling range). Product specifications in the US (ASTM), Europe (EN), and other regions employ limits on these individual properties, as well as limits on property combinations (for example, the ASTM Driveability Index originally consisted of a linear combination of three distillation temperatures) which have been indexed against observed CS&W driveability performance across the preponderance of vehicles and conditions in which the fuels are employed.

The introduction of bio-components to the gasoline blending pool (most notably ethanol at 10 vol % in the US) precipitated a revision of gasoline volatility specifications to ensure acceptable CS&W driveability. Specifically the ASTM Driveability Index which is employed in the United States was modified to include a term for ethanol content as:

$$\text{ASTM Driveability Index (DI)} = 1.5T_{10} + 3T_{50} + T_{90} + 2.4\text{EtOH} \quad \text{(Eq. 1)}$$

where $T_{10}$, $T_{50}$, and $T_{90}$ are the observed temperatures in ° F. for the distillation of 10, 50 and 90 volume percent of the fuel in a standard ASTM D86 distillation test and EtOH is the fuel's ethanol concentration in volume percent. Inclusion of the ethanol term was found to produce an improved index for the observed performance of vehicles in controlled CS&W driveability tests. The specifications establish a maximum value of DI for each seasonal volatility class; fuels with DI above the specification maximum are expected to have degraded CS&W performance.

In European applications, the EN228 gasoline specification controls mid-range volatility for good CS&W driveability by specifying a minimum volume percent E100 of the fuel that must be distilled by 100° C. in the standard distillation test.

Previous control experiments indicate that CS&W driveability performances can be problematic for gasoline blends that contain a high concentration of a butanol isomer. It was also found that existing methods for predicting CS&W driveability performance from fuel volatility parameters, such as the aforesaid Driveability Index (Eq. 1) are ineffective for high-butanol blends. Baustian, U.S. patent application Ser. No. 12/431,217, filed Apr. 28, 2009, discloses a method for producing a gasoline blend having a high concentration of at least one butanol isomer which comprises maintaining at least 35 volume percent the volume fraction of the blend that distills at temperatures up to about 200° F. However, using prior methods to blend a high concentration of butanol with gasoline under various conditions in a way that improves cold start and warm-up (CS&W) driveability, while maximizing renewable fuel component blending, was not understood. Therefore, it is highly desirable to develop a modified driveability index and method that affords the production of butanol gasoline blends that can contain high levels of at least one biologically-sourced butanol isomer, and in particular, isobutanol, while also maximizing both the CS&W driveability and the renewable components of the butanol gasoline blends.

SUMMARY OF THE INVENTION

In one aspect, the present invention is a method for producing a butanol gasoline blend having good cold start and warm-up (CS&W) driveability performance comprising: (a) blending at least one biologically-sourced butanol isomer with gasoline to form a butanol gasoline blend, the butanol gasoline blend having a specific ASTM D4814 Table 1 vapor pressure/volatility class; wherein the butanol gasoline blend has a high butanol driveability index (HBDI$_a$) value equal to the linear combination BuOH(A$_1$+A$_2$E200+A$_3$RVP) below the maximum limit for driveability index (DI) for the specific class of gasoline as specified in Table 1 of ASTM D 4814; wherein BuOH is the concentration in volume percent of the at least one biologically-sourced butanol isomer in the butanol gasoline blend; E200 is the volume percent of the butanol gasoline blend that distills at temperatures up to about 200° F.; RVP is the Reid Vapor Pressure in psi; and A$_1$, A$_2$, and A$_3$ are coefficients selected to give a substantially linear relationship between the values of the linear combination for the butanol gasoline blend containing the at least one butanol isomer and the logarithms of the mean corrected measured total weighted demerits for such blends, at concentrations of the at least one biologically-sourced butanol isomer up to about 80 volume percent; and wherein the total weighted demerits of the butanol gasoline blend is less than about 40.

In another aspect, the present invention is also a butanol gasoline blend having good cold start and warm-up (CS&W) driveability performance comprising: gasoline; and at least one biologically-sourced butanol isomer, wherein the butanol gasoline blend has a specific ASTM D4814 Table 1 vapor pressure/volatility class; and the butanol gasoline blend has a HBDI$_a$ value equal to the linear combination BuOH (A$_1$+A$_2$E200+A$_3$RVP) below the specified maximum limit for DI for the specific class of gasoline as specified in Table 1 of ASTM D 4814-09b, wherein BuOH is the concentration in volume percent of the at least one biologically-sourced butanol isomer in the butanol gasoline blend; E200 is the volume percent of the butanol gasoline blend that distills at temperatures up to about 200° F.; RVP is the Reid Vapor Pressure in psi; and A$_1$, A$_2$, and A$_3$ are coefficients selected to give a substantially linear relationship between the values of the linear combination for the butanol gasoline blend containing the at least one butanol isomer and the logarithms of the mean corrected measured total weighted demerits for such blends, at concentrations of the at least one biologically-sourced butanol isomer up to about 80 volume percent; and wherein the total weighted demerits of the butanol gasoline blend is less than about 40.

In another aspect, the invention is a method for producing a butanol gasoline blend for conventional vehicles having good cold start and warm-up (CS&W) driveability performance comprising: (a) blending at least one biologically-sourced butanol isomer with gasoline to form a butanol gasoline blend; the butanol gasoline blend having a specific ASTM D4814 Table 1 vapor pressure/volatility class; wherein the butanol gasoline blend has a high butanol driveability index (HBDI$_b$) value equal to the linear combination DI+BuOH(44−0.61E200−0.83Rvp), wherein BuOH is the concentration in volume percent of the at least one biologically-sourced butanol isomer in the butanol gasoline blend; E200 is the volume percent of the butanol gasoline blend that distills at temperatures up to about 200° F.; RVP is the Reid Vapor Pressure in psi; DI is the Driveability Index for said class of gasoline as specified in Table 1 of ASTM D 4814-09b; and the HBDI$_b$ value is lower than about 1400; and wherein the total weighted demerits of the butanol gasoline blend is less than about 40.

In another aspect, the invention is also a butanol gasoline blend for conventional vehicles having good cold start and warm-up (CS&W) driveability performance comprising: gasoline; and at least one biologically-sourced butanol isomer, wherein the butanol gasoline blend has a specific ASTM D4814 Table 1 vapor pressure/volatility class; and the butanol gasoline blend has a HBDI$_b$ value equal to the linear combination DI+BuOH(44−0.61E200−0.83Rvp), wherein: BuOH is the concentration in volume percent of the at least one biologically-sourced butanol isomer in the butanol gasoline blend; E200 is the volume percent of the butanol gasoline blend that distills at temperatures up to about 200° F.; RVP is the Reid Vapor Pressure in psi; and DI is the Driveability Index for the class of gasoline as specified in Table 1 of ASTM D 4814-09b, wherein the HBDI$_b$ value is lower than about 1400; and wherein the total weighted demerits of the gasoline blend is less than about 40.

In another aspect, the invention is a method for producing a butanol gasoline blend for conventional vehicles having good cold start and warm-up (CS&W) driveability performance comprising: (a) blending at least one biologically-sourced butanol isomer with gasoline to form a butanol gasoline blend, the butanol gasoline blend having a specific ASTM D4814 Table 1 vapor pressure/volatility class; wherein the butanol gasoline blend has a Design Variable Index (DVI) value equal to BuOH(9.69−0.146E200−0.212 Rvp), wherein BuOH is the concentration in volume percent of the at least one biologically-sourced butanol isomer in the blend; E200 is the volume percent of the butanol gasoline blend that distills at temperatures up to about 200° F.; RVP is the Reid Vapor Pressure in psi; wherein the DVI value is lower than about 75, and the total weighted demerits of the gasoline blend is less than about 40.

In another aspect, the present invention is a butanol gasoline blend for conventional vehicles having good cold start and warm-up (CS&W) driveability performance comprising: gasoline; and at least one biologically-sourced butanol isomer, wherein the butanol gasoline blend has a specific ASTM D4814 Table 1 vapor pressure/volatility class, and said the butanol gasoline blend has a DVI value equal to BuOH (9.69−0.146E200−0.212 Rvp), wherein BuOH is the concentration in volume percent of the at least one biologically-sourced butanol isomer in the blend; E200 is the volume percent of the butanol gasoline blend that distills at temperatures up to about 200° F.; RVP is the Reid Vapor Pressure in psi; wherein the DVI value is lower than about 75, and the total weighted demerits of the gasoline blend is less than about 40.

In another aspect, the invention is a method of identifying a butanol gasoline blend having good cold start and warm-up (CS&W) driveability performance comprising: (a) blending gasoline with butanol to form a butanol gasoline blend; (b) measuring fuel variables $T_{10}$, $T_{50}$, and $T_{90}$, E200 and RVP for the butanol gasoline blend; (c) inputting the fuel variables in an equation DI+BuOH(44−0.61E200−0.83Rvp) to calculate an $HBDI_b$ value of the butanol gasoline blend; wherein BuOH is the concentration in volume percent of at least one biologically-sourced butanol isomer in the butanol gasoline blend; $T_{10}$ is the temperature in ° F. for distillation of 10-volume percent of the butanol gasoline blend in a standard ASTM D86 distillation test; $T_{50}$ is the temperature in ° F. for distillation of 50-volume percent of the butanol gasoline blend in a standard ASTM D86 distillation test; $T_{90}$ is the temperature in ° F. for distillation of 90-volume percent of the butanol gasoline blend in a standard ASTM D86 distillation test; E200 is the volume percent of the butanol gasoline blend that distills at temperatures up to about 200° F.; RVP is the Reid Vapor Pressure in psi; DI is the Driveability Index for said class of gasoline as specified in Table 1 of ASTM D 4814; wherein the butanol gasoline blend has a $HBDI_b$ value lower than about 1400.

In another aspect, the invention is a method of identifying a butanol gasoline blend for conventional vehicles having good cold start and warm-up (CS&W) driveability performance comprising: (a) blending gasoline with butanol to form a butanol gasoline blend; (b) measuring fuel variables E200 and RVP for the butanol gasoline blend; (c) inputting the fuel variables in an equation BuOH(9.69−0.146E200−0.212 Rvp) to calculate a Design Variable Index (DVI) value of the butanol gasoline blend; wherein BuOH is the concentration in volume percent of at least one biologically-sourced butanol isomer in the blend; E200 is the volume percent of the butanol gasoline blend that distills at temperatures up to about 200° F.; RVP is the Reid Vapor Pressure in psi; wherein the butanol gasoline blend has a DVI value lower than about 75.

DETAILED DESCRIPTION OF THE INVENTION

Unless defined otherwise, all technical and scientific terms used herein have the same meaning as commonly understood by one of ordinary skill in the art to which this invention belongs. In the case of a conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers may be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The terms "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value; in another embodiment, within 5% of the reported numerical value.

The term "substantial" and "substantially" as used herein, means a deviation of up to 10%, preferably up to 5% is allowed.

The term "alcohol" as used herein refers to any of a series of hydroxyl compounds, the simplest of which are derived from saturated hydrocarbons, having the general formula $C_nH_{2n+1}OH$. Examples of alcohol include ethanol and butanol.

The term "butanol" as used herein, refers to n-butanol, 2-butanol, isobutanol, tert-butyl alcohol, individually or any mixtures thereof. The butanol can be biologically-sourced (i.e., biobutanol), for example. Biologically-sourced refers to fermentative production. See, e.g., U.S. Pat. No. 7,851,188, herein incorporated by reference in its entirety.

The terms "renewable component" as used herein, refers to a component that is not derived from petroleum or petroleum products.

The term "fuel" as used herein, refers to any material that can be used to generate energy to produce mechanical work in a controlled manner. Examples of fuels include, but are not limited to, biofuels (i.e., fuels which are in some way derived from biomass), gasoline, gasoline subgrades, diesel and jet fuel. It is understood that the specific components and allowances of suitable fuels can vary based on seasonal and regional guidelines.

The terms "fuel blend" or "blended fuel" as used herein, refer to a mixture containing at least a fuel and one or more alcohols.

The term "gasoline" as used herein, generally refers to a volatile mixture of liquid hydrocarbons that can optionally contain small amounts of additives. This term includes, but is not limited to, conventional gasoline, oxygenated gasoline, reformulated gasoline, biogasoline (i.e., gasoline which in some way is derived from biomass), and Fischer-Tropsch gasoline, and mixtures thereof. Additionally, the term "gasoline" includes a gasoline blend, gasoline blends, blended gasoline, a gasoline blend stock, gasoline blend stocks, and mixtures thereof. It is understood that the specific components and allowances of suitable gasolines can vary based on seasonal and regional guidelines.

The terms "gasoline blend" and "blended gasoline" as used herein, refer to a mixture containing at least a gasoline and/or gasoline subgrade and/or mixtures of one or more refinery gasoline blending components (e.g., alkylate, reformate, FCC naphthas, etc) and optionally, one or more alcohols. A gasoline blend includes, but is not limited to, an unleaded gasoline suitable for combustion in an automotive engine.

The terms "American Society for Testing and Materials" and "ASTM" as used herein, refer to the international standards organization that develops and publishes voluntary consensus technical standards for a wide range of materials, products, systems, and services, including fuels.

The term "octane rating" as used herein, refers to the measurement of the resistance of a fuel to auto-ignition in spark ignition internal combustion engines or to the measure of a fuel's tendency to burn in a controlled manner. An octane rating can be a research octane number (RON) or a motor octane number (MON). RON refers to the measurement determined by running the fuel in a test engine with a variable compression ratio under controlled conditions, and comparing the results with those for mixtures of iso-octane and n-heptane. MON refers to the measurement determined using a similar test to that used in RON testing, but with a preheated fuel mixture, a higher engine speed, and ignition timing adjusted depending on compression ratio. RON and MON are determined by standard test procedures described in the ASTM D2699 and ASTM D2700, respectively.

The fuel classes described herein are defined by the specifications for gasolines set forth in ASTM D 4814 and EN228 and vary based on a number of parameters affecting volatility and combustion such as weather, season, geographic location and altitude. Gasolines produced in accordance with ASTM D 4814 are broken into vapor pressure/distillation classes AA, A, B, C, D and E, and vapor lock protection classes 1, 2, 3, 4, 5, and 6, each class having a set of specifications describing gasolines meeting the requirements of the respective classes. Gasolines produced in accordance with EN228 are broken into volatility classes A, B, C/C1, D/D1, E/E1, and F/F1, each class having a set of specifications describing gasolines meeting the requirement of the respective classes.

The total weighted demerits of a gasoline blend is a measurement of cold start and warm up driveability performance according to the Coordinating Research Council (CRC) Cold-Start and Warm-up Driveability Procedure CRC Designation E-28-94. In this procedure, the vehicle is driven from a cold start through a set of acceleration/deceleration maneuvers by a trained rater who gives a severity rating (trace, moderate, heavy, extreme) to any driveability malfunctions observed during the maneuvers (stall, idle roughness, backfire, hesitation, stumble, surge). The severity ratings are used to calculate a total weighted demerit (TWD) for the vehicle at the test condition. The higher the TWD value, the poorer the CS&W driveability performance of the gasoline blend.

Gasolines are well-known in the art and generally contain as a primary component a mixture of hydrocarbons having different boiling points that typically boil at a temperature in the range of from about 79° F. to about 437° F. under atmospheric pressure. This range is approximate and can vary depending upon the actual mixture of hydrocarbon molecules present, the additives or other compounds present (if any), and the environmental conditions. Oxygenated gasolines are blends of one or more gasoline blend stocks and one or more oxygenates. Oxygenates are compounds or mixtures of compounds that comprise approximately 99 weight percent of which are composed of carbon, hydrogen and oxygen, with oxygen comprising at least about 5 weight percent thereof. Typically oxygenates are alcohols, ethers and mixtures thereof.

Gasoline blend stocks can be produced from a single component, such as the product from a refinery alkylation unit or other refinery streams. However, gasoline blend stocks are more commonly blended using more than one component. Gasoline blend stocks are combined to make gasoline that meet desired physical and performance characteristics and meet regulatory requirements, and may involve a few blending components. For example, a gasoline blending stock may have two to four blending components, or may have numerous blending components, such as more than four components.

Gasolines and gasoline blend stocks optionally may include other chemicals or additives. For example, additives or other chemicals can be added to adjust properties of a gasoline to meet regulatory requirements, add or enhance desirable properties, reduce undesirable detrimental effects, adjust performance characteristics, or otherwise modify the characteristics of the gasoline. Examples of such chemicals or additives include detergents, antioxidants, stability enhancers, demulsifiers, corrosion inhibitors, metal deactivators, and others. More than one additive or chemical can be used.

The term "adjusting" as used herein includes changing concentrations of the components, eliminating components, adding components, or any combination thereof so as to modify the boiling characteristics/volatility.

Useful additives and chemicals are described in Colucci et al., U.S. Pat. No. 5,782,937, which is incorporated herein by reference. Such additives and chemicals are also described in Wolf, U.S. Pat. No. 6,083,228, and Ishida et al., U.S. Pat. No. 5,755,833, both of which are incorporated by reference herein. Gasolines and gasoline blend stocks may also contain solvents or carrier solutions which are often used to deliver additives into a fuel. Examples of such solvents or carrier solutions include, but are not limited to, mineral oil, alcohols, aromatic naphthas, synthetic oils, and numerous others which are known in the art.

Gasoline blend stocks suitable for use in the method of this invention are typically blend stocks useful for making gasolines for consumption in spark ignition engines or in other engines which combust gasoline. Suitable gasoline blend stocks include blend stocks for gasolines meeting ASTM D 4814 and blend stocks for reformulated gasoline. Suitable gasoline blend stocks also include blend stocks having low sulfur content which may be desired to meet regional requirements, for example, having less than about 150, less than about 140, less than about 130, less than about 120, less than about 110, less than about 100, less than about 90, less than about 80, less than about 70, less than about 60, less than about 50, less than about 40, or less than about 30 parts per million parts by weight of sulfur. Such suitable gasoline blend stocks also include blend stocks having low aromatics content which may be desirable to meet regulatory requirements, for example having less than about 8000, less than about 7750, less than about 7500, less than about 7250, or less than about 7000 parts per million parts by volume of benzene, or, for example, having less than about 35, less than about 34, less than about 33, less than about 32, less than about 31, less than about 30, less than about 29, less than about 28, less than about 27, less than about 26, or less than about 25 volume percent total of all aromatic species present.

An oxygenate such as ethanol can also be blended with the gasoline blending stock. In that case, the resulting gasoline blend includes a blend of one or more gasoline blending stocks and one or more other suitable oxygenates. In another embodiment, one or more butanol isomers can be blended with one or more gasoline blending stocks and, optionally, with one or more suitable oxygenates such as ethanol. In such embodiment, one or more gasoline blend stocks, one or more butanol isomers and optionally one or more other suitable oxygenates can be blended in any order. For example, a butanol can be added to a mixture, including a gasoline blend stock and other suitable oxygenates. As another example, one or more other suitable oxygenates and a butanol can be added in several different locations or in multiple stages. For further examples, a butanol, such as isobutanol, n-butanol, or tert-butanol, can be added with the other suitable oxygenates, added before the other suitable oxygenates or blended with the other suitable oxygenates before being added to a gasoline blend stock. In another embodiment, a butanol, such as isobutanol, is added to oxygenate gasoline. In another embodiment, one or more other suitable oxygenates and a butanol can be blended into a gasoline blend stock contemporaneously.

In any such embodiment one or more butanol isomers and optionally one or more other suitable oxygenates can be added at any point within the distribution chain. For example, a gasoline blend stock can be transported to a terminal, and then a butanol and optionally one or more other suitable oxygenates can be blended with the gasoline blend stock, individually or in combination, at the terminal.

As a further example, the one or more gasoline blending stocks, one or more butanol isomers and optionally one or more other suitable oxygenates can be combined at a refinery. Other components or additives can also be added at any point in the distribution chain. Furthermore, the method of the present invention can be practiced at a refinery, terminal, retail site, or any other suitable point in the distribution chain.

In an embodiment of the invention, the total weighted demerits of the gasoline blend is below about 40, below about 35, below about 30, below about 25, below about 20, below about 15, or below about 10.

In an embodiment of the invention, the $HBDI_b$ value of the gasoline blend is below about 1400, below about 1350, below about 1300, below about 1250, or below about 1200.

In an embodiment of the invention, the DVI value of the gasoline blend is below about 75, below about 70, below about 65, below about 60, below about 55, below about 50, below about 45, below about 40, or below about 35.

When butanol is included in high amounts in many probable gasoline/butanol blends that would otherwise appear to meet current ASTM and EU volatility specification limits, the cold-start and warm-up (CS&W) driveability performance can be significantly deteriorated. However, it has been surprisingly and unexpectedly found that when butanol is included in gasoline/butanol blends in high amounts, the negative deterioration associated with CS&W driveability performance is avoided by the methods described herein.

In particular, 29 fuels with isobutanol concentrations ranging from 20 to 60 volume percent were tested for volatility properties and CS&W performance using industry standard methods (for example, ASTM standard distillation and vapor pressure fuel inspection tests, CRC E28 standard cold-start and warm-up driveability tests). The fuels were divided among three vehicle fleets, which included conventional and flexible fuel vehicles (FFV). The number and volatility class of fuels tested for CS&W performance, the butanol contents of the fuels in volume percent, the number, type and model years of light duty vehicles employed in the tests, and the temperatures at which tests were conducted are presented in Table 1. Table 1 also shows the number of tests that were replicated to gain statistical power. A total of 364 CS&W evaluations were conducted. The fuel blends tested on the fleets of conventional vehicles were formulated to meet ASTM D 4814-09b gasoline vapor pressure specification. The fuel blends tested on the fleet of FFV's were formulated to meet the vapor pressure specifications of either ASTM D 4814-09b or ASTM D 5798-09b fuel ethanol (Ed75-Ed85). Standards for fuel ethanol (also known as "E85" in the summer and "E70" in the winter) for sale within the United States are generally set forth in ASTM Standard Specification Number D 5798-09b ("ASTM D 5798") which is incorporated by reference herein. In Europe, no specification for E85 fuels currently exists. However, the German specification DIN 51625 issued in 2008: "Kraftstoffe für Fahrzeuge—Ethanolkraftstoff—Anforderungen and Prüfverfahren" ("Automotive fuels—ethanol fuel—Requirements and Test Methods") and defines different seasonal grades containing from 70 to 85 vol % of ethanol with a vapor pressure of Class A (summer) 35.0-60.0 kPa and Class B (winter) 50.0-90.0 kPa.

TABLE 1

| FLEET | 1 | | 2 | | 3 | |
|---|---|---|---|---|---|---|
| No. of vehicles employed | 6 | | 6 | | 6 | |
| Type of vehicles | Conventional | | Conventional | | Flexible Fuel Vehicles | |
| Vehicle Model Years (No. of vehicles) | 2005 (1), 2007 (2), 2008 (3) | | 2005 (1), 2006 (1), 2007 (4) | | 2006 (2), 2007 (2), 2008 (2) | |
| No. of Tests | 82 | 95 | 66 | 49 | 30 | 42 |
| No. of Repeat Tests | 24 | 35 | 0 | 1 | 0 | 4 |
| Fuel classes tested (based on RVP specification) | ASTM D 4814 Class AA ("Summer") | ASTM D 4814 Class D ("Winter") | ASTM D 4814 Classes AA, A ("Summer") | ASTM D 4814 Class D ("Winter") | ASTM D 5798 Class 1 ("Summer") | ASTM D 5798 Class 3 or ASTM D 4814 Class ("Winter") |
| vol % butanol | 30, 40, 50 | 30, 40, 45, 50 | 20, 30, 40, 50, 60 | 20, 30, 40, 50 | 30, 37, 40, 45, 48, 50 | 30, 37, 45, 48, 50 |
| No. of fuels tested | 4 | 5 | 5 | 4 | 6 | 5 |
| Test temps, F.: | 40, 70 | 20, 40 | 20, 30, 40, 50, 60, 70 | 20, 30, 40, 60 | 40, 70 | 5, 23, 40 |
| Mean TWD | 25.2 | | 35.8 | | 25.1 | |

Figure 1:
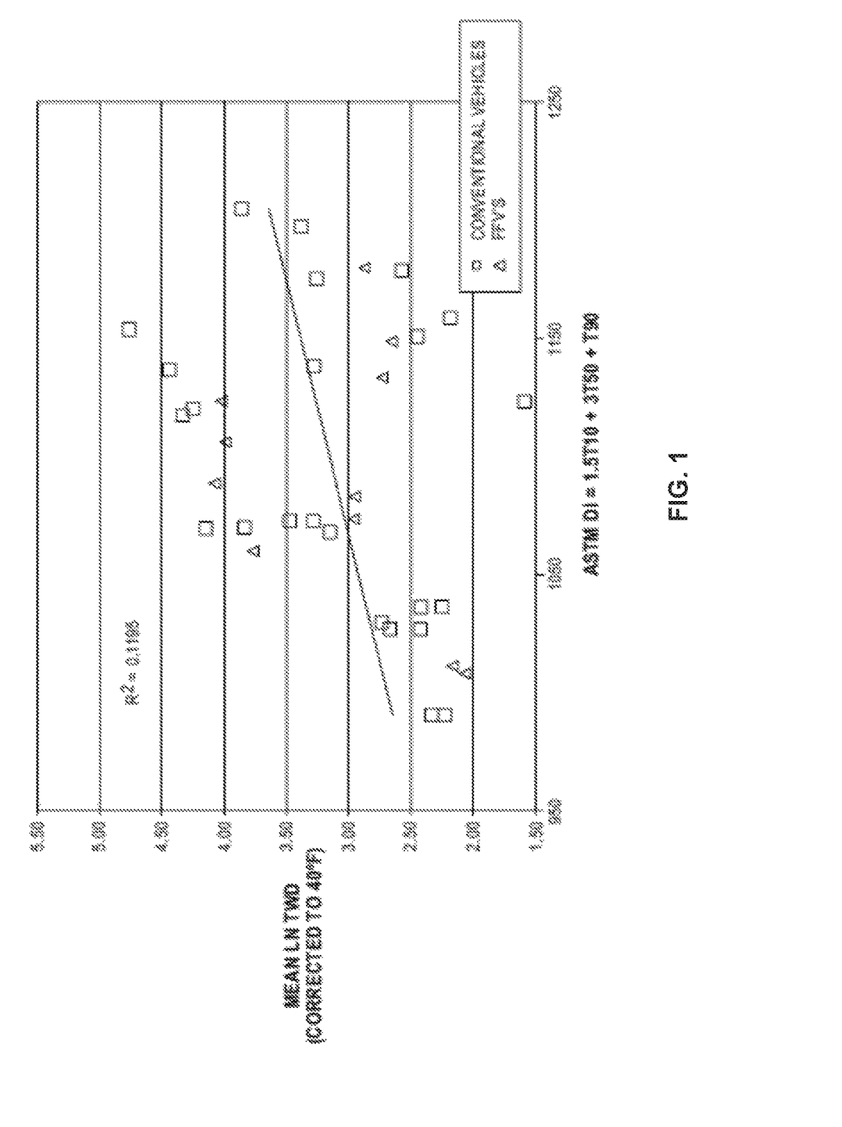
FIG. 1 is a plot of the mean corrected (to 40° F.) natural logarithm of total weighted demerits of high butanol gasoline driveability versus ASTM DI.

These tests were performed in an all-weather chassis dynamometer (max power: 315 hp, max speed: 90 mph, max. wind speed: 90 mph) with tight temperature and humidity control. The cold weather driveability tests were conducted according to the Coordinating Research Council (CRC) Cold-Start and Warm-up Driveability Procedure CRC Designation E-28-94, modified for implementation on a chassis dynamometer. In this procedure, the vehicle is driven from a cold start through a set of acceleration/deceleration maneuvers by a trained rater who gives a severity rating (trace, moderate, heavy, extreme) to any driveability malfunctions observed during the maneuvers (stall, idle roughness, backfire, hesitation, stumble, surge). The severity ratings are used to calculate a total weighted demerit (TWD) for the vehicle at the test condition. Analysis of the TWD results was patterned after a similar program conducted by the Coordinating Research Council (CRC Program CM-138-02, documented as CRC Report No. 638); the objective of the CRC Program was to establish the volatility/composition effect of low-ethanol (less than 10 volume percent) gasolines on CS&W driveability. The subject CRC Program established that Equation 1 above, wherein an ethanol "offset" term was added to the prior definition of ASTM driveability index, DI, does describe the CS&W driveability performance of gasoline blends that contain such low concentrations of ethanol. FIG. 1 is a plot of the mean corrected (to 40° F.) natural logarithms of total weighted demerits for the gasoline blends tested versus the ASTM DIs for those blends. FIG. 1 presents driveability results for the high butanol fuels tested and indexed using Equation 1. As is evident, both graphically and from the calculated fit statistic, $R^2$, Equation 1 fails to describe the CS&W driveability performance of the high-butanol fuels.

The mean corrected (to 40° F.) natural logarithms of the total weight demerits (TWD) in the figures of the application are calculated from the fleet data for all of the CS&W tests. They represent an unbiased average performance of a fuel in the vehicle fleet employed. In addition to tests of all of the fuel and vehicle combinations, additional tests that were replicates of some of those combinations were also performed. Thus, a total of 364 tests were performed. The corrected mean is the least squares mean of each fuel that is balanced as though the same number of tests were performed on each fuel-vehicle combination. This affords an unbiased TWD for each fuel averaged over all of the vehicles.

The customary driveability index DI presented as Equation 1 was replaced by the following equation, as applied to both conventional and flex fuel vehicles. Equations 2a and 2b below present the High-Butanol Driveability Index or $HBDI_a$, which is a modification of the ASTM DI, and is a linear combination of terms.

$$HBDI_a = BuOH(A_1 + A_2 E200 + A_3 RVP) \quad \text{(Eq. 2a)}$$

wherein $HBDI_a$ is the modified driveability index; BuOH is the volume percent of the at least one butanol isomer, which is preferably biologically-sourced, in the blend; E200 is the volume percent of the blend that distills at temperatures up to 200° F.; and $A_1$, $A_2$, and $A_3$ are coefficients selected to afford a substantially linear relationship between the values of the aforesaid linear combination for gasoline blends containing the at least one biologically-sourced butanol isomer and the logarithms of the measured least-square-mean corrected total weighted demerits for such blends, wherein the total weighted demerits of the gasoline blend is less than about 50, at concentrations of the at least one biologically-sourced butanol isomer up to 80 volume percent, up to 75 volume percent, up to 70 volume percent, up to 65 volume percent, up to 60 volume percent, up to 55 volume percent, up to 50 volume percent, up to 45 volume percent, or up to 40 volume percent.

In one embodiment, the high butanol driveability index ($HBDI_a$) can be determined before blending the gasoline and the at least one biologically-sourced butanol isomer, to form the butanol gasoline blend. In another embodiment, the high butanol driveability index ($HBDI_a$) can be determined after blending the gasoline and the at least one biologically-sourced butanol isomer, to form the butanol gasoline blend. If the $HBDI_a$ is determined afterwards, the gasoline amount, the at least one biologically-sourced butanol isomer amount, or any combination thereof, can optionally be adjusted so that the $HBDI_a$ has a value equal to the linear combination $BuOH(A_1 + A_2 E200 + A_3 RVP)$ below the maximum limit for driveability index (DI) for the specific class of gasoline as specified in Table 1 of ASTM D 4814. In yet another embodiment, the high butanol driveability index ($HBDI_a$) can be determined during blending the gasoline and the at least one biologically-sourced butanol isomer, to form the butanol gasoline blend. If the $HBDI_a$ is determined during blending, the gasoline amount and the at least one biologically-sourced butanol isomer amount, or any combination thereof, can optionally be adjusted so that the $HBDI_a$ has a value equal to the linear combination $BuOH(A_1 + A_2 E200 + A_3 RVP)$ below the maximum limit for driveability index (DI) for the specific class of gasoline as specified in Table 1 of ASTM D 4814. Of course, the high butanol driveability index (HBDI$_a$) can be determined once or more than once, and can be determined at various stages of blending the butanol gasoline blend, including, but not limited to, before, during, and after the butanol gasoline blend is produced.

When the concentration of the at least one biologically-sourced butanol isomer is up to 70 volume percent, $A_1$, $A_2$, and $A_3$ equal approximately 100.2, −1.5, and −2.4 respectively, and Equation 2a becomes:

$$HBDI_a = BuOH(100.2 - 1.5\ E200 - 2.4 RVP) \quad \text{(Eq. 2b)}$$

Figure 2:
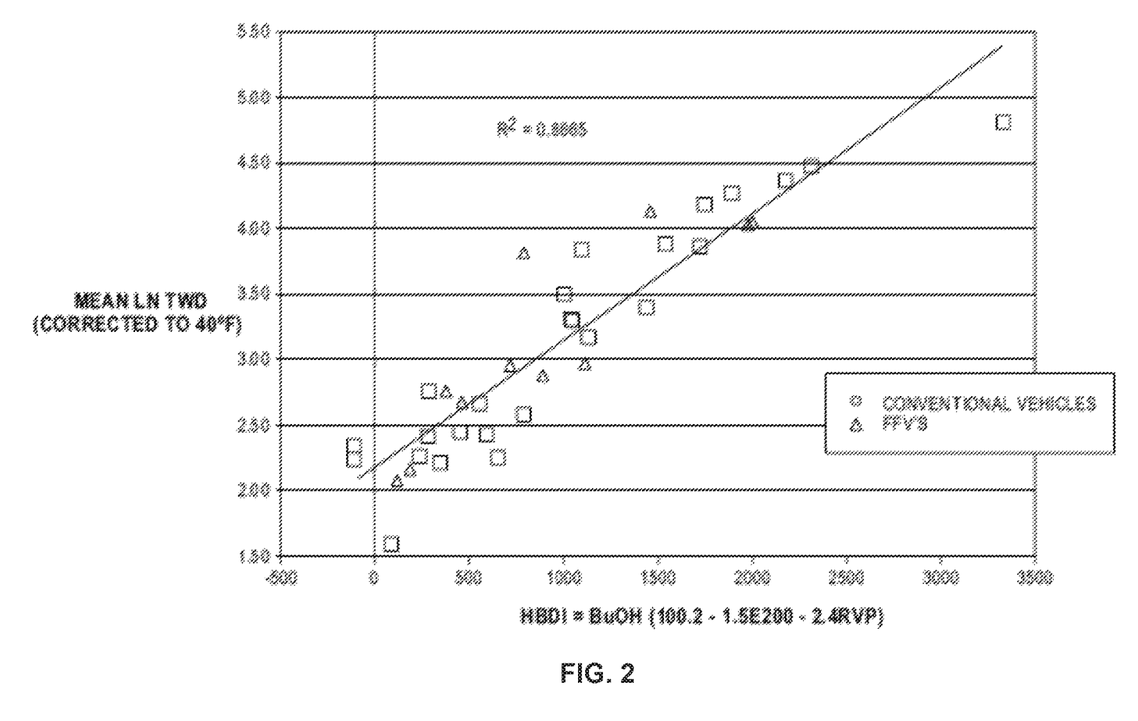
FIG. 2 is a plot of the mean corrected (to 40° F.) natural logarithm of total weighted demerits of high butanol gasoline driveability versus $HBDI_a$.
Figure 3:
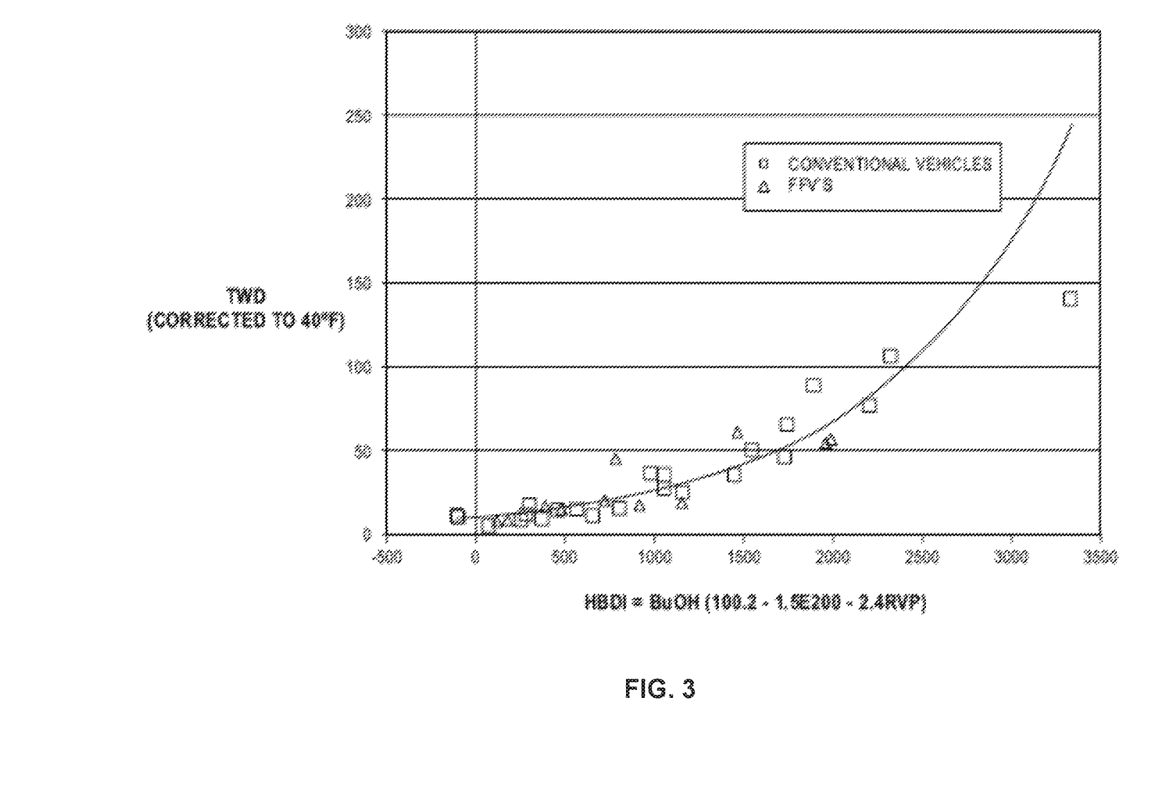
FIG. 3 is a re-plot of the data plotted in FIG. 2, except that the mean corrected (to 40° F.) total weighted demerits rather than their log transforms are plotted on the y-axis.

Eqs. 2a-2b are significantly more effective than Eq. 1 in correlating the CS&W driveability results for the high butanol fuels as shown in FIGS. 2 and 3. FIG. 2 establishes the efficacy of Eqs. 2a-2b in describing the CS&W driveability performance of high-butanol gasolines from volatility and composition properties. To demonstrate that the current specification limits from ASTM D 4814 are appropriate for the new index, the data of FIG. 2 are re-plotted without the log transform in FIG. 3.

The general method to determine the coefficients $A_1$, $A_2$ and $A_3$ for the full range of butanol concentrations up to 70 volume percent is similar to that used to determine the ethanol offset by the CRC program (CRC Program CM-138-02, CRC Report No. 638) referenced hereinabove. Briefly this method involves developing a regression equation relating natural logarithm of TWD measured by the CRC E28 standard CS&W test to corresponding fuel variables. The fuel variables E200, RVP and iBuOH were employed to derive a correlation that fit the data within the variability of the test method, and the values of the correlation coefficients for these fuel variables were calculated according to the least squares method using a general linear statistical model. In particular, the iBuOH content was added as a linear term, and E200 and RVP were added as interaction terms (i.e. iBuOH*E200 and iBuOH*RVP). FIG. 2 shows the good correlation for this semi-logarithmic relation. Coefficients for other butanol isomers may be derived by performing CS&W tests using fuels containing the isomer of interest at various concentrations and statistically analyzing the results (i.e. natural logarithm of TWD) using a general linear statistical model with factors: butanol isomer concentration and E200*butanol isomer concentration and RVP*butanol isomer concentration.

It has also been discovered that the HBDI$_a$ of a blend of gasoline with at least one biologically-sourced butanol isomer can be maintained below, or reduced to a level below, the specified maximum for that class of gasoline by adding a sufficient volume of a light hydrocarbon to the blend. Such light hydrocarbons serve to modify the boiling temperature distribution of the blend so as to improve evaporation/combustibility of the fuel in a cold engine. Some refinery streams that could be employed as such light hydrocarbons are listed in Table 2. In one embodiment, the hydrocarbons used form azeotropes with the oxygenates in the gasoline blend, namely, butanol isomers. Such azeotropes boil at even lower temperatures than the specific hydrocarbon which is added to the blend and which is a component of the azeotrope. Thus, the added light hydrocarbon that forms the azeotrope has a greater effect of reducing the boiling point of the blend than would be expected from the boiling point of the added hydrocarbon itself. Suitable such hydrocarbons and the boiling points of their azeotropes with ethanol and each butanol isomer are shown in Table 3. The word "zeotrope" in Table 3 indicates that no azeotrope was formed. In Table 3, Wt. % is the weight percent of the hydrocarbon in the azeotrope. Preferably suitable light hydrocarbons contain from 5 to 9 carbon atoms and comprise either at least one refinery stream having T90s less than 260° F. and comprising paraffins, cycloparaffins, olefins or aromatic compounds or mixtures thereof or at least one hydrocarbon that forms azeotropes with butanol or ethanol, which boil at or below 216° F. or mixtures thereof or both thereof.

TABLE 2

| Stream Name | Approximate Distillation, ° F. | | | Major Chemical types |
|---|---|---|---|---|
| | T10 | T50 | T90 | |
| Isomerate | 116 | 130 | 160 | branched C5-C6 paraffins |
| Light virgin naphtha | 95 | 130 | 180 | C5-C8 paraffins, cycloparaffins, olefins, aromatics |
| Light straight run naphtha | 95 | 130 | 180 | C5-C8 paraffins, cycloparaffins, olefins, aromatics |
| Light catalytically cracked naphtha | 110 | 140 | 250 | C5-C8 paraffins, cycloparaffins, olefins, aromatics |
| Light hydrocracked naphtha | 110 | 130 | 175 | C5-C8 paraffins, cycloparaffins, aromatics |
| Light hydrotreated coker naphtha | 115 | 140 | 200 | C5-C8 paraffins, cycloparaffins, aromatics |
| Light hydrotreated naphtha | 115 | 140 | 200 | C5-C8 paraffins, cycloparaffins, aromatics |
| Light alkylate | 165 | 215 | 230 | C6-C9 branched paraffins |
| Light reformate | 150 | 190 | 240 | C7-C8 aromatics |
| Raffinate | 150 | 180 | 240 | C6-C9 paraffins, cycloparaffins |

TABLE 3

| Hydrocarbon | Hydrocarbon Boiling Pt. (° C.) | Azeotrope with Isobutanol | | Azeotrope with n-butanol | | Azeotrope with 2-butanol | | Azeotrope with t-butanol | | Azeotrope with ethanol | |
|---|---|---|---|---|---|---|---|---|---|---|---|
| | | B. Pt. (° C.) | Wt. % | B. Pt. (° C.) | Wt. % | B. Pt. (° C.) | Wt. % | B. Pt. (° C.) | Wt. % | B. Pt. (° C.) | Wt. % |
| n-pentane | 36.1 | | | | | | | | | 34.3 | 95 |
| cyclopentane | 36.15 | | | | | | | | | 44.7 | 92.5 |
| n-hexane | 68.9 | 68.3 | 97.5 | 68.2 | 96.8 | | | 63.7 | 78 | 58.68 | 79 |
| methyl cyclopentane | 72 | 71 | 95 | | | 69.7 | 88.5 | 66.6 | 74 | | |
| benzene | 80.1 | 79.3 | 92.6 | zeotrope | | 78.5 | 84.6 | 73.95 | 63.4 | 67.9 | 68.3 |
| cyclohexane | 80.75 | 78.3 | 86 | 79.8 | 90.5 | 76 | 82 | 71.2 | 65.8 | 64.8 | 70.8 |
| cyclohexene | 82.7 | 80.5 | 85.8 | 82 | 95 | | | | | | |
| n-heptane | 98.45 | 90.8 | 73 | 93.85 | 82 | 88.1 | 63.3 | 78 | 38 | | |

TABLE 3-continued

| Hydrocarbon | Hydrocarbon Boiling Pt. (° C.) | Azeotrope with Isobutanol B. Pt. (° C.) | Wt. % | Azeotrope with n-butanol B. Pt. (° C.) | Wt. % | Azeotrope with 2-butanol B. Pt. (° C.) | Wt. % | Azeotrope with t-butanol B. Pt. (° C.) | Wt. % | Azeotrope with ethanol B. Pt. (° C.) | Wt. % |
|---|---|---|---|---|---|---|---|---|---|---|---|
| 2,2,4-trimethyl pentane | 99.3 | 92 | 73 | | | 88 | 66.2 | | | | |
| methyl cyclohexane | 100.8 | 92.6 | 68 | 95.3 | 80 | 89.7 | 61.8 | 78.8 | 34 | | |
| 2,5-dimethyl hexane | 109.2 | 98.7 | 58 | | | | | 81.5 | 23 | | |
| toluene | 110.7 | 101.2 | 55 | 105.5 | 72.2 | 95.3 | 45 | zeotrope | | 76.7 | 32 |
| cis-1,3-dimethyl cyclohexane | 120.7 | 102.2 | 44 | | | | | | | | |
| n-octane | 125.75 | | | 108.45 | 54.8 | | | | | 77 | 22 |
| ethyl benzene | 136.15 | 107.2 | 20 | 115.85 | 34.9 | | | | | zeotrope | |
| p-xylene | 138.4 | 107.1 | 11.4 | 115.7 | 32 | | | zeotrope | | zeotrope | |
| m-xylene | 139 | | | 116.5 | 28.5 | | | | | | |
| o-xylene | 143.6 | | | 116.8 | 25 | | | | | | |
| n-nonane | 150.7 | | | 115.9 | 28.5 | | | | | | |

The data in Tables 4 and 5 illustrate the benefit in the reduction of $HBDI_a$ achieved by the addition of light hydrocarbons to the blend. In Table 4, the HBDIs for blends containing 50 volume percent of i-butanol (iB50,$) with either a combination of 20 volume percent of n-pentane (Pen) and 20 volume percent of alkylate (alk) (iB50+Pen20+Alk 20, s) or 20 volume percent of only n-pentane (iB50+Pen20, s) are substantially reduced from over 2200 to below 1250, accompanied by a substantial reduction for TWD at 5° F. in one vehicle (EU FFV#2) from over 250 to below 20. By contrast, the data in Table 5 illustrate that the addition of 26 volume percent of branched hydrocarbons (HC), which had a higher boiling point than the gasoline component of the blend that it replaced, produced essentially no benefit in the reduction of $HBDI_a$ or TWD. In Table 4 and 5, s and S mean a summer grade, and w and W mean a winter grade.

In another experiment, ten unique test fuels were developed in order to satisfy the parameters shown in Table 6 below:

TABLE 6

| Factor | High | Low |
|---|---|---|
| i-BuOH | 30 vol % | 50 vol % |
| Rvp | 7.5 psi | 12 psi |
| E200 | 20 vol % | 50 vol % |

Each of the ten fuels were tested for their driveability characteristics. Six light-duty vehicles meeting US Tier 2 emission standards were used for the driveability/volatility evaluations. Vehicles were selected so as to provide a variety of Tier 2 technology types including both natural and forced induction, port- and direct-injection, and Tier 2 emissions certifications from Bin 8, Bin 5, and even one California PZEV (about Bin 2). General descriptions of the test vehicles appear in Table 7 below.

TABLE 4

| Fuel | Iso-butanol vol % | E200 Vol % | RVP, psi | $HBDI_a$ | EU FFV#1 at 5° F. | 23° F. | 41° F. | EU FFV#2 at 5° F. | 23° F. | 41° F. |
|---|---|---|---|---|---|---|---|---|---|---|
| iB40.w | 40 | 31.5 | 8.9 | 1326 | 27 | | | 20 | | |
| iB50.w | 50 | 27.3 | 8.5 | 2012 | 22 | | | 239, 429 | 211 | 117 |
| iB60.w | 60 | 18.8 | 6.9 | 3386 | 144 | 58 | 31 | | | |
| iB70.w | 70 | 15.8 | 6.1 | 4396 | 105 | 147 | 125 | | | |
| iB50, s | 50 | 27.7 | 6.1 | 2279 | 27 | | | 259 | | |
| iB50 + Pen20 + Alk20, s | 50 | 36.9 | 9.7 | 1177 | 0 | | | 15 | | |
| iB50 + Pen20, s | 50 | 37.9 | 10.3 | 986 | 0 | | | 6 | | |

TABLE 5

| Fuel | Iso-butanol vol % | E200 vol % | Rvp, psi | $HBDI_a$ | TWD@40 F. |
|---|---|---|---|---|---|
| S-6 | 48 | 30.0 | 6.46 | 1984 | 57 |
| S-7 | 50 + 26% HC | 28.2 | 8.3 | 1978 | 56 |
| S-9 | 45 | 39.7 | 7.51 | 1114 | 19 |
| W-6 | 48 | 32.5 | 9.51 | 1461 | 61 |
| W-7 | 45 | 44.4 | 13.37 | 180 | 9 |
| W-8 | 50 | 44.0 | 14.31 | 117 | 8 |

TABLE 7

| Vehicle ID | Year | Make | Model | Engine | FIE | Emissions Cert |
|---|---|---|---|---|---|---|
| 5-DO-1 | 2005 | Dodge | Neon | 2.0 I-4 | PFI | T2 B8 |
| 7-FO-1 | 2007 | Ford | Edge | 3.5 V-6 | PFI | T2 B5 |
| 7-TO-1 | 2007 | Toyota | Camry | 3.5 V-6 | PFI | T2 B5 |
| 8-CV-3 | 2008 | Chevrolet | HHR | 2.0 I-4 TAC | DI | T2 B5 |

TABLE 7-continued

| Vehicle ID | Year | Make | Model | Engine | FIE | Emissions Cert |
|---|---|---|---|---|---|---|
| 8-FO-1 | 2008 | Ford | Focus | 2.0 I-4 | PFI | PZEV |
| 8-MA-2 | 2008 | Mazda | CX-7 | 2.3 I-4 TAC | DI | T2 B5 |

Driveability tests were conducted in the All-weather Chassis Dynamometer (AWCD) facility at GFT's Naperville site. Vehicles were instrumented with HEM DAWN/Snap-Master OBD-II data acquisition systems for monitoring engine and vehicle operating parameters at about 2 Hz/channel during the tests. All vehicles were serviced and inspected prior to beginning the test program. None of the vehicles presented prompt or pending diagnostic trouble codes. In preparation for each driveability test, the subject vehicle fuel system was thoroughly flushed and filled with test fuel. After checking and clearing ECU trouble codes set by the fuel flushing process, each vehicle was conditioned on the Naperville test track for thirty minutes to allow the engine management system to adjust fuelling for the varying oxygen content of the test fuels.

Driveability evaluations were conducted according to CRC E-28-94 Cold-start and Warm-up Driveability Test Procedure as adapted for use in an all-weather chassis dynamometer test cell. In order to explore the effect of temperature on driveability performance, each vehicle/fuel combination was tested at two temperatures: winter fuels (Class D, 12 psi Rvp) were tested at 20 and 40 F, while summer fuels (Class AA, 7.5 psi Rvp) were tested at 40 and 70 F. With sixteen fuels (including replicates) tested among 6 vehicles at two temperatures, the total of number of E28 tests conducted for the driveability/volatility study reached 192.

The test fuel recipes are shown in the Table 8 below:

TABLE 8

| Fuel | | DAN | SHN | LUF | HCN | ICN | Alky T | Alky M | HUF | Toluene | nC4 | UltS | UltW | UltE | EtOH | i-BuOH |
|---|---|---|---|---|---|---|---|---|---|---|---|---|---|---|---|---|
| Driveability/ | 00 | | 15 | | 29 | | | | | 20.5 | 5.5 | | | | 30 | |
| Volatility | 01 | 20 | | 15 | 5 | | 28.5 | | | | 1.5 | | | | 30 | |
| Test Fuels | 02 | | 28.5 | 19 | | | | | | | 2.5 | | | | 50 | |
| | 03 | | | 35 | | 15 | | | | | | | | | 50 | |
| | 04 | | | | 42 | | | | 15 | | 13 | | | | 30 | |
| | 05 | 20 | | 19 | 10 | | 12 | | | | 9 | | | | 30 | |
| | 06 | | | 12.8 | 19.6 | | 8.8 | | | | 9.8 | | | | 49 | |
| | 07 | | | | | 27 | | | | | 2 | | 26 | | 45 | |
| | 08 | 10 | 15 | 20 | | | 13.5 | | | | 1.5 | | | | 40 | |
| | 09 | 10 | | 16 | 15 | | 9.5 | | | | 9.5 | | | | 40 | |
| | 10 | 10 | 15 | 20 | | | 13.5 | | | | 1.5 | | | | 40 | |
| | 11 | 20 | | 15 | 5 | | 28.5 | | | | 1.5 | | | | 30 | |
| | 12 | | 22.8 | 15.2 | | | | | | | 2 | | | 20 | 40 | |
| | 13 | 10 | | 16 | 15 | | 9.5 | | | | 9.5 | | | | 40 | |
| | 14 | | | 12.8 | 19.6 | | 8.8 | | | | 9.8 | | | | 49 | |
| | 15 | 20 | | 19 | 10 | | 12 | | | | 9 | | | | 30 | |

Descriptions of the blending components in Table 8 are shown in Table 9, below.

TABLE 9

| Blendstock | Full Name | Source | Description |
|---|---|---|---|
| DAN | De-butanized Absorber | BP Whiting refinery | FCCU light naphtha |
| SHN | Stabilized Heavy Naphtha | BP Whiting refinery | FCCU heavy naphtha |
| HCN | Heavy Cat Naphtha | BP Carson refinery | FCCU heavy naphtha |
| ICN | Iso-Cracker Naphtha | BP Toledo refinery | iso-cracker light naphtha |
| LUF | Light UltraFormate | BP Whiting refinery | light reformate |
| HUF | Heavy UltraFormate | BP Whiting refinery | heavy reformate |
| Alky T | Light Alkylate | BP Toledo refinery | re-run alkylate |
| Alky M | Alkylate | Amoco Mandan Producer's Chemical | alkylate |
| Toluene | toluene | | solvent-grade toluene |
| nC4 | n-butane | Aeropres | n-butane |
| UltS | Ultimate | BP Rochelle terminal | Ultimate gasoline - summer |
| UltW | Ultimate | BP Rochelle terminal | Ultimate gasoline - winter |
| UltE | Ultimate | BP Rochelle terminal | Ultimate E10 gasoline -- |

CRC E28 tests of cold-start and warm-up driveability are scored in a demerit system. As the vehicle is started and driven over the controlled cycle, driveability faults such as long crank time, stalling, hesitation, etc. are observed and scored for severity by the trained rater operating the test. The observed demerits are compiled over the test through a standard objectionability weighting system into an overall score of Total Weighted Demerits, or TWD. The rater also assigns an overall subjective rating ranging from 10 (no faults) to 0 (extreme faults), though these ratings are not typically nor herein use in analysis or conclusions. Of the planned 192 driveability evaluations, 189 were completed over a nine-week period. Three tests with the Mazda CX-7 were aborted due to extreme startability problems. Results from the driveability evaluations are compiled in Table 10 below.

TABLE 10

| Fuel ID | Test Temp, F. | 5-DO-1 TWD | 5-DO-1 Rating | 7-FO-1 TWD | 7-FO-1 Rating | 7-TO-1 TWD | 7-TO-1 Rating | 8-CV-3 TWD | 8-CV-3 Rating | 8-FO-1 TWD | 8-FO-1 Rating | 8-MA-2 TWD | 8-MA-2 Rating |
|---|---|---|---|---|---|---|---|---|---|---|---|---|---|
| 00 | 40 | 39.5 | 4 | 62.5 | 3 | 38 | 4 | 60 | 3 | 67 | 3 | 35 | 5 |
| 00 | 70 | 31.5 | 5 | 46 | 4 | 43 | 4 | 12.5 | 7 | 30 | 5 | 16 | 7 |
| 01 | 40 | 15 | 7 | 10.5 | 9 | 6 | 9 | 8.5 | 8 | 7.5 | 9 | 32 | 5 |
| 01 | 70 | 12 | 8 | 7 | 9 | 7 | 9 | 8 | 9 | 7 | 9 | 7 | 9 |
| 02 | 40 | 40 | 6 | 46 | 4 | 51.5 | 4 | 58.5 | 4 | 64 | 4 |  |  |
| 02 | 70 | 43.5 | 4 | 29 | 5 | 38 | 4 | 13 | 8 | 25 | 5 | 116 | 2 |
| 03 | 40 | 14 | 8 | 16.5 | 6 | 15.5 | 9 | 24.5 | 4 | 14.5 | 9 | 139.5 | 3 |
| 03 | 70 | 17 | 7 | 9 | 8 | 9.5 | 8 | 9 | 8 | 10 | 9 | 68 | 3 |
| 04 | 20 | 55 | 3 | 33.5 | 4 | 34 | 4 | 105 | 3 | 22 | 6 | 256 | 1 |
| 04 | 40 | 27 | 5 | 43 | 4 | 23.5 | 5 | 30.5 | 4 | 19.5 | 5 | 23.5 | 5 |
| 05 | 20 | 16 | 8 | 8 | 9 | 7 | 9 | 15 | 8 | 9 | 8 | 46 | 5 |
| 05 | 40 | 9.5 | 8 | 6.5 | 9 | 8.5 | 9 | 16 | 8 | 6.5 | 9 | 11 | 8 |
| 06 | 20 | 109 | 3 | 196.5 | 2 | 278 | 1 | 104.5 | 2 | 97 | 3 |  |  |
| 06 | 40 | 42 | 5 | 47.5 | 4 | 36.5 | 5 | 54.5 | 4 | 52.5 | 5 | 343 | 0 |
| 07 | 20 | 22.5 | 8 | 10 | 8 | 19 | 7 | 11 | 8 | 8 | 9 | 256.5 | 1 |
| 07 | 40 | 11 | 8 | 14 | 8 | 8.5 | 8 | 9.5 | 8 | 7 | 8 | 157 | 1 |
| 08 | 40 | 12 | 8 | 23.5 | 5 | 12 | 7 | 21.5 | 5 | 25 | 5 | 206 | 2 |
| 08 | 70 | 13 | 8 | 8 | 9 | 7 | 9 | 8 | 9 | 9 | 9 | 60 | 4 |
| 09 | 20 | 20 | 8 | 25.5 | 5 | 12.5 | 8 | 33.5 | 4 | 10.5 | 8 | 268 | 1 |
| 09 | 40 | 9 | 8 | 13 | 8 | 12 | 7 | 11.5 | 8 | 7 | 9 | 17.5 | 5 |
| 10 | 40 | 33 | 6 | 20.5 | 6 | 14.5 | 8 | 12 | 8 | 36 | 5 | 303.5 | 2 |
| 10 | 70 | 23 | 7 | 9 | 8 | 9 | 8 | 9.5 | 8 | 9 | 8 | 12.5 | 9 |
| 11 | 40 | 13.5 | 7 | 6.5 | 9 | 7 | 9 | 14 | 8 | 12.5 | 9 | 7 | 9 |
| 11 | 70 | 12 | 8 | 7 | 9 | 7 | 9 | 9.5 | 8 | 7.5 | 9 | 8 | 9 |
| 12 | 40 | 57 | 5 | 57.5 | 4 | 57.5 | 3 | 83 | 2 | 92 | 3 |  |  |
| 12 | 70 | 48 | 5 | 36.5 | 4 | 43 | 4 | 14.5 | 8 | 37 | 4 | 269 | 0 |
| 13 | 20 | 16 | 7 | 13 | 7 | 16 | 8 | 25 | 6 | 10 | 8 | 259.5 | 1 |
| 13 | 40 | 15 | 8 | 12.5 | 8 | 7.5 | 8 | 9.5 | 8 | 6.5 | 9 | 110.5 | 3 |
| 14 | 20 | 124.5 | 3 | 77 | 3 | 143 | 3 | 93 | 2 | 153 | 2 | 375 | 0 |
| 14 | 40 | 21 | 7 | 56.5 | 3 | 38 | 4 | 44 | 4 | 32 | 4 | 171.5 | 0 |
| 15 | 20 | 14 | 8 | 8.5 | 9 | 8 | 9 | 20.5 | 6 | 10 | 8 | 21 | 8 |
| 15 | 40 | 9.5 | 8 | 12.5 | 8 | 9.5 | 8 | 11.5 | 8 | 11.5 | 8 | 8 | 8 |

Standard analysis of driveability results begins with calculation of least-square-mean (LSM) corrected responses for total weighted demerits. This technique is used to remove variations due to non-fuel factors, e.g., vehicle, test temperature, etc. The result is a single value of LSM corrected TWD for each fuel which can then be modeled against fuel variables. Standard linear regression techniques were employed to develop models relating driveability to fuel properties. In each case, fuel properties were regressed on the log-transform Fuel LSM TWD responses (hereafter represented as $TWD_{LSM}$). Several model forms were evaluated including straightforward regressions using the experimental design variables, standard models employing distillation properties (e.g., the ASTM Driveability Index), and variations of the standard models.

Statistical analyses were performed on the data generated from the driveability experiments. The analysis began by combining the customary DI factor along with the experimental design variables i-BuOH, E200, and Rvp and all possible interactions. The best correlation was obtained by including DI, i-BuOH, and the two-factor interactions of i-BuOH with E200 and Rvp. The model incorporating these results is:

$$\ln(TWD_{LSM}) = 0.00197 \text{ DI} + i\text{-BuOH}(0.087 - 0.0012 \text{ E200} - 0.0016 \text{ Rvp}) \quad \text{(Eq. 3)}$$

Normalizing the right-hand-side of Eq (3) to achieve a unity coefficient for DI results in the following index expression for $HBDI_b$:

$$HBDI_b = DI + BuOH(44 - 0.61 E200 - 0.83 Rvp) \quad \text{(Eq. 2c)}$$

wherein BuOH is the concentration in volume percent of the at least one biologically-sourced butanol isomer in the blend; E200 is the volume percent of the blend that distills at temperatures up to about 200° F.; RVP is the Reid Vapor Pressure in psi; DI is the Driveability Index for said class of gasoline as specified in Table 1 of ASTM D 4814-09b; wherein the concentrations of the at least one biologically-sourced butanol isomer are up to about 80 volume percent, up to about 75 volume percent, up to about 70 volume percent, up to about 65 volume percent, up to about 60 volume percent, up to about 55 volume percent, up to about 50 volume percent, up to about 45 volume percent, or up to about 40 volume percent.

Another model for driveability were developed by simply evaluating the experimental design variables iso-butanol concentration (i-BuOH), D86 evaporated fraction at 200° F. (E200), and vapor pressure (Rvp) as regressors. Factor effect tests showed the most effective form of this model to include iso-butanol and its interaction with the other two variables. The final form of this model is:

$$\ln(TWD_{LSM}) = 2.275 + i\text{-BuOH}(0.0969 - 0.00146 \text{ E200} - 0.00212 \text{ Rvp}) \quad \text{(Eq. 4)}$$

The final term in Eq (4) forms the basis for an "index" in the fuel properties; such an index can be useful for designing fuels with good driveability. Multiplying the final term through by 100 for convenience, the Design Variable Index (DVI) is given by Eq (2d):

$$(DVI) = i\text{-BuOH}(9.69 - 0.146 E200 - 0.212 Rvp) \quad \text{(Eq. 2d)}$$

wherein i-BuOH is the concentration in volume percent of iso-butanol isomer in the blend; E200 is the volume percent of the blend that distills at temperatures up to about 200° F.; RVP is the Reid Vapor Pressure in psi; wherein the concentrations of the at least one biologically-sourced butanol isomer are up to about 80 volume percent, up to about 75 volume percent, up to about 70 volume percent, up to about 65 volume percent, up to about 60 volume percent, up to about 55 volume percent, up to about 50 volume percent, up to about 45 volume percent, or up to about 40 volume percent.

The index $HBDI_b$ or DVI is employed by inserting distillation and vapor pressure test data for a subject fuel in the equation and calculating the value of the new index. The resulting value calculated from Eqs. 2c or 2d is then compared to the maximum value of about 1400 for $HBDI_b$, or about 75 for DVI. If the calculated $HBDI_b$ or DVI are below these levels, the fuel will have acceptable CS&W performance.

The HBDI and DVI model were validated using a new set of splash-blended high-butanol fuels. Properties for the fuels in the validation data were used to calculate predicted TWD using both the HBDI and DVI models; results of these calculations are listed in Table 11 below and presented graphically in FIGS. 4 and 5.

TABLE 11

| Fuel | Observed Driveability, LSM corrected to 40 F. | | Fuel Properties | | | Design Variable Model, LSMs predicted at 40 F. | | | $HBDI_b$ Model, LSMs predicted at 40 F. | | |
|---|---|---|---|---|---|---|---|---|---|---|---|
| | ln TWD | TWD | i-BuOH, vol % | DI | E200, Vol % | Rvp, Psi | DVI | ln TWD | TWD | HBDI | ln TWD | TWD |
| S1230 | 2.66 | 14.3 | 0 | 1228 | 39.2 | 8.63 | 0 | 2.275 | 9.7 | 1228 | 2.420 | 11.2 |
| S00 | 2.16 | 8.6 | 0 | 1167 | 44.8 | 8.77 | 0 | 2.275 | 9.7 | 1167 | 2.299 | 10.0 |
| S20 | 2.25 | 9.4 | 20 | 1159 | 44.3 | 7.86 | 31 | 2.587 | 13.3 | 1369 | 2.710 | 15.0 |
| S30 | 2.82 | 16.8 | 30 | 1179 | 38.5 | 7.43 | 75 | 3.023 | 20.6 | 1609 | 3.189 | 24.3 |
| S40 | 3.37 | 29.1 | 40 | 1197 | 33.0 | 6.92 | 136 | 3.637 | 38.0 | 1922 | 3.812 | 45.2 |
| S50 | 4.43 | 84.2 | 50 | 1137 | 26.0 | 6.37 | 227 | 4.548 | 94.4 | 2280 | 4.521 | 91.9 |
| S60 | 4.96 | 142.6 | 60 | 1154 | 21.0 | 5.83 | 323 | 5.508 | 246.6 | 2735 | 5.422 | 226.3 |
| W122 | 2.68 | 14.5 | 0 | 1213 | 40.5 | 12.3 | 0 | 2.275 | 9.7 | 1213 | 2.391 | 10.9 |
| W00 | 2.11 | 8.2 | 0 | 1093 | 50.0 | 13.53 | 0 | 2.275 | 9.7 | 1093 | 2.154 | 8.6 |
| W20 | 1.91 | 6.8 | 20 | 1124 | 46.2 | 12.02 | 8 | 2.353 | 10.5 | 1240 | 2.459 | 11.7 |
| W30 | 2.62 | 13.7 | 30 | 1151 | 40.6 | 11.18 | 42 | 2.692 | 14.8 | 1449 | 2.879 | 17.8 |
| W40 | 3.31 | 27.4 | 40 | 1175 | 34.0 | 10.27 | 102 | 3.296 | 27.0 | 1766 | 3.508 | 33.4 |
| W50 | 4.24 | 69.3 | 50 | 1120 | 27.4 | 9.27 | 186 | 4.138 | 62.7 | 2100 | 4.171 | 64.8 |
| W60 | 5.03 | 153.6 | 60 | 1144 | 20.6 | 8.46 | 294 | 5.212 | 183.5 | 2610 | 5.180 | 177.8 |

As seen from Table 11, both the $HBDI_b$ and DVI models are good predictors of ln TWD of the fuel blends.

Figure 4:
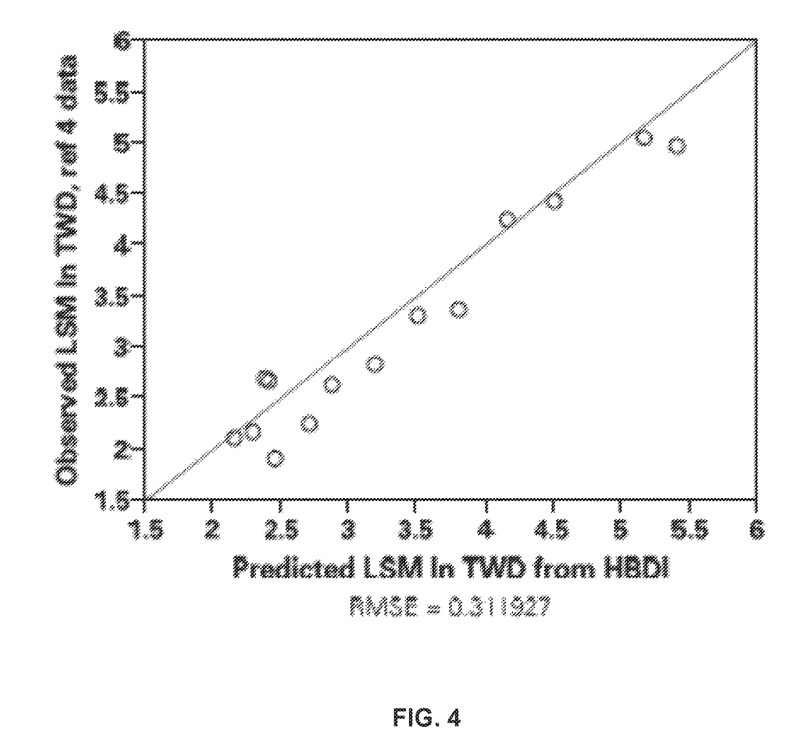
FIG. 4 is a correlation of the observed LSM ln TWD with the predicted LSM ln TWD using the $HBDI_b$ equation 2c.
Figure 5:
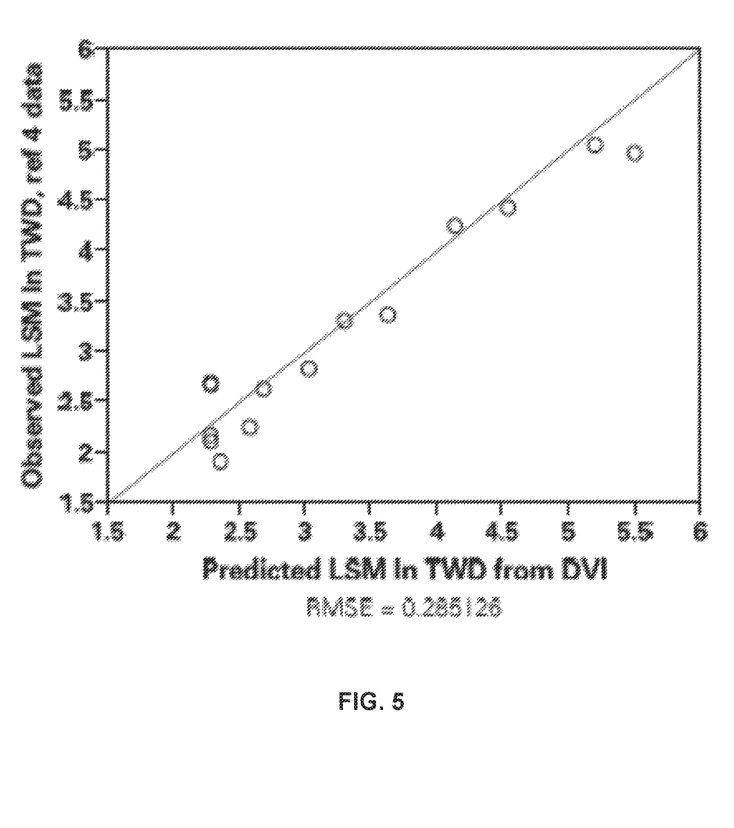
FIG. 5 is a correlation of the observed LSM ln TWD with the predicted LSM ln TWD using the DVI equation 2d.

The predictive value of the $HBDI_b$ and DVI models is also shown in FIG. 4 and FIG. 5. FIG. 4 demonstrates the efficacy of Equation 2c in predicting TWD for high butanol fuels using their $HDBI_b$ values. FIG. 5 demonstrates the efficacy of Equation 2d in predicting TWD for high butanol fuels using their DVI values.

The data in Table 11 FIGS. 4 and 5 span fuels for conventional vehicles with iso-butanol concentrations up to about 60 volume percent, and also span the range of driveability performance from acceptable to unacceptable. Based on the results, it can be concluded that a limit of 1400 maximum $HBDI_b$ for A-class fuels is appropriate for fuels that contain up to 60 volume percent of isobutanol, the isobutanol preferably being biologically-sourced. It is also readily apparent that the fuels containing up to 60 volume percent of isobutanol, which is preferably biologically-sourced, can be formulated using 75 DVI as a limit and achieve the same low demerit level as conventional butanol-free fuels indexed to 1250 DI.

Those skilled in the art would readily appreciate that, if other measures of the volatility or boiling point profile, such as E158, of a gasoline blend were employed instead of E200, this would result in relatively minor variations of Equations 2a-2b, but the claimed method and gasoline blend of this invention would extend to and include such variations.

It will be appreciated by those skilled in the art that although the present invention has been described herein by reference to specific means, materials and examples, the scope of the present invention is not limited thereto, and extends to all other means and materials suitable for the practice of this invention.

What is claimed is:

1. An isobutanol gasoline blend for conventional vehicles having good cold start and warm-up (CS&W) driveability performance comprising:
    gasoline;
    a biologically-sourced isobutanol wherein the concentration of isobutanol is 40-80 volume percent of the gasoline blend,
        blended so the isobutanol gasoline blend has a specific ASTM D4814 Table 1 vapor pressure/volatility class; and a High Butanol Driveability Index (HBDI$_b$) value determined by the equation: DI+BuOH (44−0.61E200−0.83RVP), wherein:
        BuOH is the concentration in volume percent of the biologically-sourced isobutanol in the isobutanol gasoline blend;
        E200 is the volume percent of the isobutanol gasoline blend that distills at temperatures up to about 200° F.;
        RVP is the Reid Vapor Pressure in psi; and
        DI is the Driveability Index for the class of gasoline as specified in Table 1 of ASTM D 4814,
    wherein the HBDI$_b$ value is lower than about 1400; and wherein the total weighted demerits of the gasoline blend is less than about 40; and
    at least one hydrocarbon in an amount that forms an azeotrope with isobutanol, wherein the hydrocarbon is n-hexane, methyl cyclopentane, cyclohexane, cyclohexene, n-heptane, 2,2,4-trimethyl pentane, methyl cyclohexane, 2,5-dimethyl hexane, toluene, cis-1,3-dimethyl cyclohexane, p-xylene, or mixtures thereof.

2. The isobutanol gasoline blend of claim 1, further comprising a sufficient volume of light hydrocarbons to adjust the value of HBDI$_b$ value below about 1400.

3. The isobutanol gasoline blend of claim 1, further comprising one or more additives.

4. The isobutanol gasoline blend of claim 3, wherein the one or more additives are detergents, antioxidants, stability enhancers, demulsifiers, corrosion inhibitors, metal deactivators, or mixtures thereof.

5. An isobutanol gasoline blend for conventional vehicles having good cold start and warm-up (CS&W) driveability performance comprising:

gasoline;

a biologically-sourced isobutanol wherein the concentration of isobutanol is 40-80 volume percent of the gasoline blend, blended so the isobutanol gasoline blend has a specific ASTM D4814 Table 1 vapor pressure/volatility class, and a Design Variable Index (DVI) value determined by the equation: BuOH (9.69−0.146E200−0.212RVP), wherein:

BuOH is the concentration in volume percent of the biologically-sourced isobutanol in the blend;

E200 is the volume percent of the isobutanol gasoline blend that distills at temperatures up to about 200° F.;

RVP is the Reid Vapor Pressure in psi;

wherein the DVI value is lower than about 75, and the total weighted demerits of the gasoline blend is less than about 40; and at least one hydrocarbon in an amount that forms an azeotrope with isobutanol, wherein the hydrocarbon is n-hexane, methyl cyclopentane, cyclohexane, cyclohexene, n-heptane, 2,2,4-trimethyl pentane, methyl cyclohexane, 2,5-dimethyl hexane, toluene, cis-1,3-dimethyl cyclohexane, p-xylene, or mixtures thereof.

6. The isobutanol gasoline blend of claim 5, wherein the isobutanol gasoline blend additionally comprises a sufficient volume of light hydrocarbons to adjust the DVI value lower than about 75.

7. The isobutanol gasoline blend of claim 5, further comprising one or more additives.

8. The isobutanol gasoline blend of claim 7, wherein the one or more additives are detergents, antioxidants, stability enhancers, demulsifiers, corrosion inhibitors, metal deactivators, or mixtures thereof.

* * * * *